United States Patent [19]

Kanno et al.

[11] Patent Number: 4,522,913

[45] Date of Patent: Jun. 11, 1985

[54] MONOACRYLATE OR DIACRYLATE OF 2-METHYL-PROPYLENE GLYCOL AND PHOTOSENSITIVE COMPOSITION CONTAINING THE DIACRYLATE

[75] Inventors: Tatsuya Kanno; Yuzo Toga, both of Himeji, Japan

[73] Assignee: Daicel Chemical Industries, Ltd., Osaka, Japan

[21] Appl. No.: 623,613

[22] Filed: Jun. 21, 1984

Related U.S. Application Data

[62] Division of Ser. No. 418,119, Sep. 14, 1982, abandoned.

[30] Foreign Application Priority Data

Sep. 17, 1981 [JP] Japan ................................ 56-147099
Sep. 28, 1981 [JP] Japan ................................ 56-153449
Sep. 28, 1981 [JP] Japan ................................ 56-153450

[51] Int. Cl.$^3$ ............................................. C08F 2/50
[52] U.S. Cl. ..................................... 430/285; 430/286; 430/288; 430/915; 204/159.16; 204/159.12; 204/159.15; 525/59; 525/502; 527/314; 560/224

[58] Field of Search ................ 526/323.1, 323.2; 204/159.16, 159.15, 159.23, 159.12; 430/285, 286, 287

[56] References Cited

U.S. PATENT DOCUMENTS

| | | | |
|---|---|---|---|
| 3,634,369 | 1/1972 | Baumann | 526/323.2 |
| 3,660,145 | 5/1972 | Johnson et al. | 525/920 |
| 3,980,627 | 9/1976 | McDowell et al. | 526/323.1 |
| 4,187,383 | 2/1980 | Cowherd et al. | 560/224 |
| 4,245,077 | 1/1981 | Demarco | 526/323.2 |

OTHER PUBLICATIONS

Chao, Ve-Hsiav et al., *Chemical Abstracts*, vol. 90, (1979), #122,634 p. and Chemical Substances Index, (1971–1981), at p. 44,373CS.

*Primary Examiner*—Allan M. Lieberman
*Assistant Examiner*—A. H. Koeckert
*Attorney, Agent, or Firm*—Flynn, Thiel, Boutell and Tanis

[57] ABSTRACT

Mono(meth)acrylate or di(meth)acrylate of 2-methylpropylene glycol. The diacrylate, or a low molecular weight oligomer thereof, with polymeric filler and sensitizer is useful as a photosensitive component.

3 Claims, No Drawings

MONOACRYLATE OR DIACRYLATE OF 2-METHYL-PROPYLENE GLYCOL AND PHOTOSENSITIVE COMPOSITION CONTAINING THE DIACRYLATE

This application is a division of U.S. Ser. No. 418,119, filed Sept. 14, 1982, now abandoned.

The invention relates to monoacrylate or monomethacrylate of 2-methylpropylene glycol, diacrylate or dimethacrylate of 2-methylpropylene glycol, a low molecular weight polymer of the diacrylate or dimethacrylate, and a photosensitive composition comprising diacrylate or dimethacrylate of 2-methylpropylene glycol and/or a low molecular weight polymer thereof.

In general, most glycol mono- or diacrylates are prepared by reacting acrylic or methacrylic acid with a glycol.

The glycols already known are ethylene glycol, diethylene glycol, triethylene glycol, tetraethylene glycol, propylene glycol, 1,3- and 1,4-butylene glycol, neopentyl glycol, 1,6-hexamethylene glycol, trimethylolpropane, pentaerythritol, or the like. The glycol monoacrylates have both a polymerizable vinyl group and an active hydroxyl group in each molecule, so they are used in quite broad applications as starting materials or intermediates for thermosetting paints, adhesives, nonwoven fabric binders, paper finishing agents, copolymer modifiers, ion exchange resins, dental materials, cross-linking agents and fiber finishing agents, but the type of glycol must be selected carefully for obtaining the most suitable glycol monoacrylate for each application.

The glycol di(meth)acrylates have two polymerizable vinyl groups in each molecule, so they are used in quite broad applications as starting materials or intermediates for thermosetting paints, adhesives, nonwoven fabric binders, photosensitive agents, paper finishing agents, copolymer modifiers and cross-linking agents, but the type of glycol must be selected carefully for obtaining the most suitable glycol di(meth)acrylate for each application.

The inventors have studied keenly to broaden the scope of selection and found that monoacrylate or diacrylate of 2-methylpropylene glycol, prepared by using 2-methylpropylene glycol as a glycol component, is a novel compound, and it possesses various characteristic properties as compared with conventional glycol monoacrylates. The present invention is based on these findings.

That is, the present invention provides novel glycol monoacrylates of the formula:

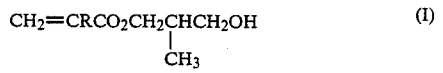

$$CH_2=CRCO_2CH_2CHCH_2OH \quad \text{(I)}$$
$$\phantom{CH_2=CRCO_2CH_2}|\phantom{CHCH_2OH}$$
$$\phantom{CH_2=CRCO_2CH_2}CH_3$$

and then novel 2-methylpropylene glycol di(meth)acrylates of the formula:

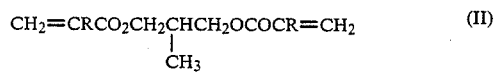

$$CH_2=CRCO_2CH_2CHCH_2OCOCR=CH_2 \quad \text{(II)}$$
$$\phantom{CH_2=CRCO_2CH_2}|\phantom{CHCH_2OCOCR=CH_2}$$
$$\phantom{CH_2=CRCO_2CH_2}CH_3$$

wherein R is hydrogen or methyl group.

Said 2-methylpropylene glycol as a glycol component of 2-methylpropylene glycol monoacrylate may be manufactured industrially by the oxidation of isobutene or by the oxo reaction of allyl alcohol. The chemical constitution of the compound is unsymmetrical about the main molecular chain owing to the presence of a 2-methyl group, and two terminal hydroxyl groups are chemically very reactive, since they are primary hydroxyl groups.

Generally, glycol monoacrylate is prepared by several synthetic methods, that is, (1) dehydrochlorination between acryloyl or methacryloyl chloride and glycol, (2) interesterification between a lower alkyl acrylate or methacrylate and glycol, and (3) direct dehydration between acrylic or methacrylic acid and glycol, except that 2-hydroxyethyl methacrylate is prepared by the reaction of methyl methacrylate with ethylene oxide.

Said 2-methylpropylene glycol monoacrylate may be synthesized by any of methods (1), (2) and (3) mentioned above. Method (1) is described below definitely as an example: 2-methylpropylene glycol and an equimolar amount of a tertiary amine such as pyridine or triethylamine were poured into a solvent selected from aromatic hydrocarbons such as benzene, toluene and xylene, aliphatic or alicyclic hydrocarbons such as hexane and cyclohexane, or ether in a reactor equipped with stirring blades, into which an equimolar amount of acryloyl or methacryloyl chloride was added dropwise gradually under stirring at 0°–10° C. The mixture was reacted sufficiently for 5–8 hours after dropping, and the formed ammonium hydrochloride was removed from the reaction mixture by filtering.

Next, the solvent was removed by reduced pressure distillation, and the residue was thereafter vacuum distilled to give 2-methylpropylene monoacrylate as the end product, which was a colorless and transparent liquid. Said compound was identified by means of infrared absorption spectrum, nuclear magnetic resonance spectrum and elementary analysis.

Generally, a glycol di(meth)acrylate is prepared by several synthetic methods, that is, (1) dehydrochlorination between acryloyl or methacryloyl chloride and glycol, (2) dehydrochlorination between a glycol monoacrylate derivative and acryloyl or methacryloyl chloride, (3) interesterification between a lower alkyl acrylate or methacrylate and glycol, and (4) direct dehydration between acrylic or methacrylic acid and glycol.

Said 2-methylpropylene glycol di(meth)acrylate may be synthesized by any of methods (1) through (4) mentioned above. Method (1) is described below definitely as an example: one mol of 2-methylpropylene glycol and two mol of a tertiary amine such as pyridine or triethylamine were poured into a solvent selected from aromatic hydrocarbons such as benzene, toluene and xylene, aliphatic or alicyclic hydrocarbons such as hexane and cyclohexane, or ether in a reactor equipped with stirring blades, into which two mols of acyloyl or methacryloyl chloride was added dropwise gradually under stirring at 0°–10° C. The mixture was reacted sufficiently for 5–8 hours after dropping, and the formed ammonium hydrochloride was removed from the reaction mixture by filtering. Next, the solvent was removed by reduced pressure distillation, and the residue was thereafter vacuum distilled to give 2-methylpropylene glycol di(meth)acrylate as the end product of colorless, transparent liquid. Said compound was identified by means of infrared absorption spectrum, nuclear magnetic resonance spectrum and elementary analysis.

The resulting monoacrylate or diacrylate of 2-methylpropylene glycol has a methyl group as a side chain in the glycol component, and therefore possesses several characteristics, that is, a polarity effect due to an electron-releasing property of the methyl group, elimination of a methyne hydrogen atom bound by a covalent bond to the same carbon atom to which the methyl group is bound and high reactivities of a terminal polymerizable double bond and a terminal hydroxyl group. It may be therefore expected to be used in broad applications such as starting materials or intermediates for thermosetting paints, adhesives and cross-linking agents and then copolymer modifiers.

Furthermore, the diacrylate may apply to photosensitive agents.

The diacrylate or dimethacrylate of 2-methylpropylene glycol may be polymerized into a low molecular weight polymer suitable for a photosensitive substance. The low molecular weight polymer of the obtained 2-methylpropylene glycol di(meth)acrylate may be obtained by the polymerization reaction carried out in the presence of an extremely small amount of an ordinary polymerization catalyst. However, it is preferred to effect the heat polymerization reaction in the absence of catalyst at 50°–100° C. for about 15–60 min. If the degree of polymerization is too high, the low polymer per se is cross-linked and hardened and becomes unsuitable for use as a constituent of the photosensitive composition. The degree of polymerization is thus up to 5, preferably up to 3.

The present invention relates also to a photosensitive composition containing a glycol diacrylate or dimethacrylate [hereinafter referred to as di(meth)acrylate] or low polymers thereof as an active ingredient. More particularly, the present invention relates to a photosensitive composition containing one compound or a mixture of two or more compounds selected from the group consisting of 2-methylpropylene glycol di(meth)acrylates and low polymers thereof as active ingredient(s).

As photosensitive high molecular monomers, there have been used generally liquid monomers having a high boiling point and good hardening properties, since they have a low flash point or toxicity and they are easily treated at ambient temperature under atmospheric pressure. As the monomers satisfying these conditions, there have been used polyfunctional monomers containing at least two unsaturated groups in the molecule and low polymers of them. Most of the unsaturated groups comprises ethylenically unsaturated groups. Numerous studies have been made on photosensitive compositions comprising polyfunctional monomers containing ethylenically unsaturated groups as the functional groups or low polymers thereof and various photosensitive compositions of this kind have been proposed. For exmaple, as the polyfunctional monomers, there may be mentioned polyhydric alcohol/acrylic acid esters, polyvalent acrylic acid esters bonded with urethane bond, unsaturated esters of polyvalent carboxylic acids and polyvalent unsaturated acid amides bonded with amido bond. Among them, almost all of the polyhydric alcohol/acrylic acid esters are liquids having a high boiling point and they per se are photopolymerized to form three-dimensional, hardened products. A solution of another high molecular substance (hereinafter referred to as filling high molecular compound) in the polyhydric alcohol/acrylic acid ester forms an excellent, hardened film and is, therefore, used as a photosensitive composition in the production of a photo-resist, paint or ultraviolet-curing ink broadly.

The photosensitive composition according to the invention comprises as active ingredient(s) one compound or a mixture of two or more compounds selected from the group consisting of 2-methylpropylene glycol di(meth)acrylates of the formula (II) and low polymers thereof (preferably those having a degree of polymerization of 2–5):

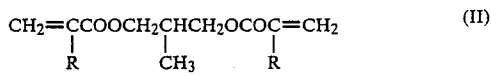

wherein R represents hydrogen or methyl group. It has a high hardening velocity and forms an image having a quite excellent resolution when it is used as a photo-resist.

In using the polyhydric alcohol/acrylic or methacrylic acid ester or its low polymer as a photopolymerizable compound used for forming a photo-resist, this compound is generally dissolved in an organic solvent together with a film-forming high-molecular filler, sensitizer, dye, etc. to form a homogeneous solution. The resulting solution is applied to a base to form a film having a proper thickness. Then, the solvent is removed to form a so-called photosensitive resin film. The film is exposed to ultraviolet ray or the like to reproduce an image by the photographic method.

It has been found that surprisingly, when the photosensitive composition containing as active ingredient(s) one compound or a mixture of two or more compounds selected from the group consisting of 2-methylpropylene glycol di(meth)acrylate and low polymers thereof is used, for example, in the production of a photo-resist, a high hardening velocity is attained and an image having an extremely high resolution can be obtained. Though reasons therefor have not fully been elucidated yet, the following two facts may be mentioned: a stable tertiary radical is formed in 2-methylpropylene glycol constituting 2-methylpropylene glycol diacrylate or dimethacrylate according to:

(1) a polarity effect obtained by the electron releasing effect of the methyl group bonded with carbon atom in the 2-position, and (2) an effect of elimination of a hydrogen atom in the 2-position due to the effect of (1).

As a result, the cross-linking effect would be further improved. In other words, it is considered that said compound behaves like a trifunctional unsaturated compound, though it has only two photo-polymerizable terminal unsaturated groups. The amount of one compound or a mixture of two or more compounds selected from the group consisting of 2-methylpropylene glycol di(meth)acrylates and low polymers thereof contained in the photosensitive composition of the present invention is 20–80 wt.%, preferably 30–60 wt.%, based on the solid content of the composition excluding the solvent.

As the high molecular fillers which can be incorporated in the photosensitive composition of the present invention, there may be mentioned a homopolymer and copolymers of methyl methacrylate, cellulose derivatives, polyvinyl alcohol and novolac resin. As the sensitizer, there may be used Michler's ketone, N,N'-tetraethyl-4,4'-diaminobenzophenone, 5-nitroacenaphthene, 1,2-benzanthraquinone, N-acetyl-4-nitronaphthylamine, benzil, benzoin, α-naphthoquinone, 1-nitropyrene, 9- fluorenone or 1,8-phthaloylnaphthalene. As a matter of course, a clear high-resolution image can be obtained also when one compound or a mixture of two or more compounds selected from the group consisting of 2-methylpropylene glycol di(meth)acrylates and low polymers thereof of the present invention is mixed with a well-known polyfunctional monomer or a low polymer thereof such as pentaerythritol triacrylate or trimethylolpropane trimethacrylate in a proper ratio.

In using the photosensitive composition of the present invention, there may be employed far ultraviolet rays, electron beams and laser beams in addition to ultraviolet rays.

The following exmaples will further illustrate the present invention, which by no means limit the invention.

Parts in the following examples are given by weight. Infrared absorption spectrum was measured by Nippon Bunko IRA-2, and nuclear magnetic resonance spectrum was measured by Nippon Denshi C-60 HL.

EXAMPLE 1

50 parts of 2-methylpropylene glycol and 56 parts of triethylamine were stirred vigorously in a dried ether solvent, and 50.5 parts of acryloyl chloride was added dropwise gradually at 0°–10° C. while the reaction vessel was cooled from outside with iced water. After dropping, the stirring was continued for five hours at ordinary temperature to confirm the completion of the reaction. Thereafter triethylamine hydrochloride was filtered off from the reaction mixture, and the filtrate was dried over anhydrous magnesium sulfate, and filtered again to remove the inorganic salt. Next, the filtrate was distilled under reduced pressure to remove ether, and 70 parts of pale yellow liquid was obtained as residue. The residue in which three parts of cuprous chloride was added as a polymerization inhibitor was vacuum distilled to give 58 parts of colorless, transparent liquid (56° C./2 mmHg). The resulting liquid product was identified as 2-methylpropylene glycol monoacrylate by means of elementary analysis, infrared absorption spectrum and nuclear magnetic resonance spectrum.

| Elementary analysis (%) | observed | theoretical |
|---|---|---|
| C | 58.01 | 58.32 |
| H | 8.62 | 8.39 |
| IR absorption spectrum | | |
| 3,100–3,650 cm$^{-1}$ | alcoholic hydroxyl group | |
| 1,715, 1,725 cm$^{-1}$ | carbonyl group of ester linkage | |
| 1,410 cm$^{-1}$ | carbonyl methyne group | |
| NMR spectrum | | |
| 5.75–6.70 ppm | olefin proton | 3H |
| 4.23 ppm | methylene proton | 4H |
| 3.5–4.0 ppm* | hydroxyl proton | 1H |
| 2.15 ppm | methyne proton | 1H |
| 1.05 ppm | methyl proton | 3H |

*disappears by heavy water exchange

EXAMPLE 2

50 parts of 2-methylpropylene glycol and 56 parts of triethylamine were stirred vigorously in a dried ether solvent, and 58 parts of methacryloyl chloride was added dropwise gradually at 0°–5° C. while the reaction vessel was cooled from outside with iced water. After dropping, the stirring was continued for five hours at ordinary temperature to confirm the completion of the reaction. Thereafter triethylamine hydrochloride was filtered off from the reaction mixture, and the filtrate was dried over anhydrous magnesium sulfate, and filtered again to remove the inorganic salt. Next, the filtrate was distilled under reduced pressure to remove ether, and 68 parts of pale yellow liquid was obtained as residue. The residue in which three parts of cuprous chloride was added as a polymerization inhibitor was vacuum distilled to give 60 parts of colorless, transparent liquid (56° C./2 mmHg). The resulting liquid product was identified as 2-methylpropylene glycol monomethacrylate by means of elementary analysis, infrared absorption spectrum and nuclear magnetic resonance spectrum.

| Elementary analysis (%) | observed | theoretical |
|---|---|---|
| C | 60.49 | 69.74 |
| H | 9.10 | 8.92 |
| IR absorption spectrum | | |
| 3,100–3,650 cm$^{-1}$ | alcoholic hydroxyl group | |
| 1,720 cm$^{-1}$ | carbonyl group of ester linkage | |
| 1,640 cm$^{-1}$ | terminal vinyl group | |
| NMR spectrum | | |
| 5.28 ppm | olefin proton | 2H |
| 4.18 ppm | methylene proton | 4H |
| 3.75–3.95 ppm* | hydroxyl proton | 1H |
| 1.96 ppm | methyl proton | 3H |
| 1.00 ppm | methyl proton | 3H |

*disappears by heavy water exchange

EXAMPLE 3

50 parts of 2-methylpropylene glycol and 101 parts of triethylamine were stirred vigorously in a dried ether solvent, and 100 parts of acryloyl chloride was added dropwise gradually at 0°–10° C. while the reaction vessel was cooled from outside with iced water. After dropping, the stirring was continued for five hours at ordinary temperature to confirm the completion of the reaction. Thereafter triethylamine hydrochloride was filtered off from the reaction mixture, and the filtrate was washed with water till it became neutral, dried over anhydrous magnesium sulfate, and filtered again. Next, the filtrate was distilled under reduced pressure to remove ether, and 102 parts of pale yellow liquid was obtained as residue. The residue in which 5 parts of cuprous chloride was added as a polymerization inhibitor was vacuum distilled to give 90 parts of colorless, transparent liquid (71° C./3 mmHg).

The resulting liquid product was identified as 2-methylpropylene glycol diacrylate by means of elementary analysis, infrared absorption spectrum and nuclear magnetic resonance spectrum.

| Elementary analysis (%) | observed | theoretical |
|---|---|---|
| C | 60.35 | 60.60 |
| H | 6.92 | 7.12 |
| IR absorption spectrum | | |
| 1720 cm$^{-1}$ | carbonyl group of ester part | |
| 1640 cm$^{-1}$ | terminal vinyl group | |
| 1420 cm$^{-1}$ | carbonylmethyl group | |
| NMR spectrum | | |
| 5.70–6.50 ppm | olefin proton | 6H |
| 4.10 ppm | methylene proton | 4H |
| 2.25 ppm | methylene proton | 1H |
| 1.05 ppm | methyl proton | 3H |

EXAMPLE 4

50 parts of 2-methylpropylene glycol and 62 parts of acrylic acid were added to 100 parts of dried benzene, into which 0.5 part of 2,6-di-t-butyl-p-cresol as a polymerization inhibitor, and 4.0 parts of p-toluenesulfonic acid as a dehydration agent were added, and the mixture was refluxed for 3–8 hours to remove water by the formation of an azeotrope. Next, the reaction mixture was washed with water till the filtrate became neutral, dried over anhydrous magnesium sulfate and filtered. The solvent was distilled off from the filtrate under reduced pressure to leave 85 parts of pale yellow liquid product. 5 parts of cuprous chloride were added to the residue as a polymerization inhibitor, and the mixture was distilled under vacuum to give 80 parts of colorless and transparent liquid product (74° C./3.5 mmHg).

The resulting liquid product exhibited the same spectrographic data as in Example 3, and was identified as 2-methylpropylene glycol diacrylate.

EXAMPLE 5

50 parts of 2-methylpropylene glycol and 116 parts of triethylamine were stirred vigorously in 100 parts of a dried ether solvent, and 116 parts of methacryloyl chloride was added dropwise gradually at 0°–5° C. while the reaction vessel was cooled from outside with iced water. After dropping, the stirring was continued for five hours at room temperature to confirm the completion of the reaction. Thereafter triethylamine hydrochloride was filtered off from the reaction mixture, and the filtrate was washed with water till it became neutral, dried over anhydrous magnesium sulfate, and filtered again. Next, the filtrate was distilled under reduced pressure to remove ether, and 110 parts of pale yellow liquid was obtained as residue. The residue into which 5 parts of cuprous chloride was added as a polymerization inhibitor was vacuum distilled to give 95 parts of colorless, transparent liquid (62° C./2 mmHg).

The resulting liquid product was identified as 2-methylpropylene glycol dimethacrylate by means of elementary analysis, infrared absorption spectrum, and nuclear magnetic resonance spectrum.

| Elementary analysis (%) | observed | theoretical |
| --- | --- | --- |
| C | 63.42 | 63.70 |
| H | 7.92 | 8.02 |
| IR absorption spectrum | | |
| 1720 cm$^{-1}$ | carbonyl group of ester linkage | |
| 1642 cm$^{-1}$ | terminal vinyl group | |
| 1420 cm$^{-1}$ | carbonylmethyne group | |
| NMR spectrum | | |
| 5.84 ppm | olefin proton | 4H |
| 4.18 ppm | methylene proton | 4H |
| 2.25 ppm | methyne proton | 1H |
| 1.95 ppm | methyl proton | 6H |
| 1.00 ppm | methyl proton | 3H |

Preparation 1

100 parts of methyl methacrylate was poured in 200 parts of dry toluene. 0.7 parts of N,N'-azobisisobutyronitrile known as a polymerization initiator was added to the mixture and the reaction was carried out at 60° C. under nitrogen atmosphere for about 5 h. After completion of the reaction, the reaction mixture was poured in methanol to precipitate a white polymer. After drying the same sufficiently, its viscosity was measured using toluene as the solvent to reveal that [η] was 0.34 (25° C.).

APPLICATION EXAMPLE 1

| | |
| --- | --- |
| Compound obtained in Example 3 | 10 parts |
| High molecular compound obtained in preparation 1 | 12.5 parts |
| Michler's ketone | 1.0 parts |
| Crystal Violet | 0.05 parts |
| Hydroquinone | 0.05 parts |
| Toluene | 50 parts |

The above liquid composition was stirred violently by means of a homogenizer for about 10 min. to uniformly disperse the pigment. The resulting coating liquid was applied on a PET film (75 mμ) by means of a Mare bar coater and dried at 60° C. for 5 min. to obtain a blue sheet. The coating layer had a thickness of about 5 μm. The resulting photosensitive film was contacted with a photographic transparent negative and exposed to a light of Orc Jet Printer (a product of Orc Seisakusho; 2 kw mercury lamp, Type JP-2000) at a distance of 40 cm from the light source for about 120 sec. Immediately after the exposure, the exposed part was colored in yellow and a latent image was recognized. Then, the development was effected using a mixture of 10 parts of toluene and 90 parts of n-hexane. The compounds in the unexposed part were removed from the PET film and those in the photo-hardened part were insolubilized and remained as they were on the PET film. The resolution of the image thus obtained was 20 μm.

APPLICATION EXAMPLE 2

| | |
| --- | --- |
| Compound obtained in Example 5 | 10 parts |
| High molecular compound obtained in Preparation 1 | 12.5 parts |
| 2,5-Di(4'-azidobenzal)cyclohexanone | 0.8 parts |
| Crystal Violet | 0.05 parts |
| Hydroquinone | 0.2 parts |
| Tetrachloroethane | 50 parts |

The above liquid composition was treated in the same manner as in Application Example 1 to disperse the pigment therein. The resulting coating liquid was applied on a PET film and dried. The coating layer had a thickness of about 5 μm. After the exposure in the same manner as in Application Example 1, a latent image was colored in reddish yellow. The development was effected using a mixture of 10 parts of tetrachloroethane, 10 parts of toluene and 80 parts of n-hexane to obtain an extremely good image. The resolution of the image thus obtained was 25 μm.

COMPARATIVE EXAMPLE 1

| | |
| --- | --- |
| Diethylene glycol diacrylate | 10 parts |
| High molecular compound obtained in Preparation 1 | 12.5 parts |
| Michler's ketone | 1.0 parts |
| Crystal Violet | 0.05 parts |
| Hydroquinone | 0.05 parts |
| Toluene | 50 parts |

The above liquid composition was treated in the same manner as in Application Example 1 to disperse the pigment therein. The resulting coating liquid was applied on a PET film and dried. The coating layer had a thickness of about 5 μm. After the exposure in the same manner as in Application Example 1, a latent image could be recognized only slightly. The development was effected using the same developing liquid (a mixture of 10 parts of toluene and 90 parts of n-hexane) as in Application Example 1 to obtain an image. The resolution of the image thus obtained was about 40 μm.

APPLICATION EXAMPLE 3 AND COMPARATIVE EXAMPLE 2, 3

In these respective example and comparative examples, 2-methylpropylene glycol diacrylate, 1,3-butylene glycol diacrylate and neopentyl glycol diacrylate were used in the same mole number and respective photosensitive coating compositions were prepared as listed in Table 1, based on parts by weight.

TABLE 1

|  | Application Example 3 | Comparative Example 2 | Comparative Example 3 |
| --- | --- | --- | --- |
| photosensitive component | 2-methylpropylene glycol diacrylate | 1,3-butylene glycol diacrylate | neopentyl glycol diacrylate |
|  | 54 | 50.2 | 57.8 |
| polymethylmethacrylate (Preparation 1) | 40 | 40 | 40 |
| benzophenone | 5.0 | 5.0 | 5.0 |
| Michler's ketone | 0.5 | 0.5 | 0.5 |
| hydroquinone | 0.05 | 0.05 | 0.05 |
| Crystal Violet | 0.45 | 0.45 | 0.45 |
| 2-butanone | 95 | 98 | 92 |

Each of the obtained coating compositions was coated on a polyethylene terephthalate sheet of 75 micron thickness so as to have a thickness of 25 microns with a Mare bar coater and then dried at 75° C. for 5 min. in order to remove out 2-butanone, the solvent. Each of the obtained photosensitive films was masked with a 15-staged tablet, manufactured by Fuji Photo Film Co., Ltd., and exposed to the light of Orc Jet Printer at a distance of 40 cm from the light source for a period of time listed in Table 2. Thereafter it was allowed to stand for 15 minutes and developed with 1,1,1-trichloroethane at the room temperature for 40 secs. The sensitivity of each photosensitive composition was determined by measuring the stage number in the developed film. Results are shown in Table 2.

TABLE 2

| sample | Comparison of the Stage Number exposure time | | | |
| --- | --- | --- | --- | --- |
|  | 10 secs. | 20 secs. | 30 secs. | 40 secs. |
| Application Example 3 | 2 | 6 | 9 | 11 |

TABLE 2-continued

| sample | Comparison of the Stage Number exposure time | | | |
| --- | --- | --- | --- | --- |
|  | 10 secs. | 20 secs. | 30 secs. | 40 secs. |
| Comparative Example 2 | 1 | 4 | 7 | 10 |
| Comparative Example 3 | 1 | 3 | 4 | 5 |

It is noted from the above mentioned results that 2-methylpropylene glycol diacrylate used in Application Example 3 is superior to Comparative examples 2 and 3 in respect to sensitivity. In addition, it was found that neopentyl glycol diacrylate had large adhesion and therefore made the used mark dirty. Furthermore it had only a slow rate of curing, the bad adhesion and an eventual disadvantage such that even the nondissolved portion was removed away on the development state.

1,3-propylene glycol diacrylate was also examined in the same way as in Comparative Examples 2 and 3. But it was not successful to proceed with the test, because it was easy to polymerize even at the room temperature, difficult to isolate and had only a very short shelf life when it had been converted to the coating composition.

The embodiments of the invention in which an exclusive property or privilege is claimed are defined as follows:

1. A photosensitive composition which comprises, as the active photopolymerizable substance, one or a mixture of two or more compounds having the formula

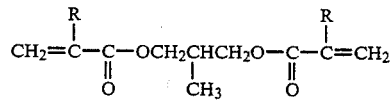

wherein R is hydrogen or methyl, or low molecular weight polymers thereof having a degree of polymerization of up to 5, said composition also containing polymeric filler and a sensitizer.

2. A photosensitive composition according to claim 1 which contains from 20 to 80% by weight of said active photopolymerizable substance, said polymeric filler is selected from the group consisting of homopolymers and copolymers of methyl methacrylate, cellulose derivatives, polyvinyl alcohol and novolac resin, and said sensitizer is selected from the group consisting of Michler's ketone, N,N'-tetraethyl-4,4'-diaminobenzophenone, 5-nitroacenaphthene, 1,2-benzanthraquinone, N-acetyl-4-nitronaphthylamine, benzil, benzoin, α-naphthoquinone, 1-nitropyrene, 9-fluorenone and 1,8-phthaloylnaphthalene.

3. A photoresist comprising a support and a light-sensitive layer coated on said support, said light-sensitive layer being made of a photosensitive composition as claimed in claim 1.

* * * * *